United States Patent [19]

Fujimoto et al.

[11] Patent Number: 5,034,987
[45] Date of Patent: Jul. 23, 1991

[54] CONTINUOUS PHOTOGRAPHING AND OBSERVING OF A THREE-DIMENSIONAL IMAGE

[75] Inventors: Masafumi Fujimoto, Tokyo; Shigeru Minakami, Yamato; Takuya Haneda, Hachiouji, all of Japan

[73] Assignee: Nippon Identograph Co., Ltd., Tokyo, Japan

[21] Appl. No.: 343,411

[22] Filed: Apr. 25, 1989

[30] Foreign Application Priority Data

Dec. 9, 1988 [JP] Japan .................. 63-309822

[51] Int. Cl.[5] ............................................. G06K 9/00
[52] U.S. Cl. .................................. 382/6; 364/413.14; 364/413.15; 364/413.16; 358/111
[58] Field of Search .................... 378/99; 358/111; 364/413.14, 413.15, 413.16; 382/6

[56] References Cited

U.S. PATENT DOCUMENTS

| | | | |
|---|---|---|---|
| 4,144,457 | 3/1979 | Albert | 364/413.15 |
| 4,544,949 | 10/1985 | Kurihara . | |
| 4,558,359 | 12/1985 | Kuperman et al. | 340/729 |
| 4,639,941 | 1/1987 | Hounsfield | 358/111 |
| 4,672,651 | 6/1987 | Horiba et al. | 378/9 |
| 4,723,261 | 2/1988 | Janssen | 358/111 |

OTHER PUBLICATIONS

*Encyclopedia of Computer Science and Engineering*, pp. 1527–1530, second edition, copyright 1983 by Van Nostrand Reinhold Co.

*Primary Examiner*—Leo H. Boudreau
*Assistant Examiner*—Steven P. Fallon
*Attorney, Agent, or Firm*—Wall and Roehrig

[57] ABSTRACT

A target is continuously observed and stereoscopic three-dimensional image information of the target is recorded. A transmitter unit irradiates a target with suitable radiation, an image recording unit records radiation images of the target, a rotating unit incrementally positions the target between the transmitting and image recording units, injecting means places a contrast material into the target, a memory stores a first set of reference images of the target for predetermined number of angular increments prior to injection of said contrast material and stores second set of contrast images for each angular increment of rotation of the target after injection of the contrast material, an arithmetic unit produces a set of drawn or subtractive images of the target from the stored reference and contrast image data, and an indicator unit displays two drawn images of the target that are separated by a certain angular difference so that the two images can be viewed in three dimension using a stereo-scope.

20 Claims, 5 Drawing Sheets

Fig. 5
CLOCKWISE ROTATION    COUNTERCLOCKWISE ROTATION
(1) 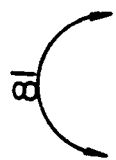
(2) 
(3) 

CONTINUOUS PHOTOGRAPHING AND OBSERVING OF A THREE-DIMENSIONAL IMAGE

BACKGROUND OF THE INVENTION

This invention relates to continuous photographing and observing a three-dimensional image, and in particular, to an apparatus for producing a high quality three-dimensional image of certain portions of a selected target using radiological imaging rays.

OBJECTS AND SUMMARY OF THE INVENTION

Using a conventional type of an apparatus for photographing and observing a three-dimensional target, two images are obtained by radiating a certain portion of a selected target from two different directions separated from each other by a predetermined angle. The two images are recorded and viewed under a stereo-scope to obtain a three-dimensional rendition of the target area. This type of conventional method allows only for the observation of a stationary target and therefore, portions of the target can only be observed three-dimensionally from a certain predetermined angle.

In responding to this need, an apparatus for continuously observing a rotational three-dimensional image of a target from a desired angle has been proposed in Japanese Patent Laid-Open Application (Kokai) No. 61-159941. An x-ray image is transmitted from a selected portion of the target and is observed three-dimensionally from a desired angle through operating a gantry which rotates the imaging equipment around the target.

The previously noted method provides a transmitted image of a certain portion of a target, such as a cerebral cavity, where a contrast material is injected into the target and is allowed to flow in and out of the target region to be observed. The transmitted image accompanied with an injected contrast material is not often used because unwanted images of tissue and bone are typically located at or close to the desired target. Furthermore, since synchronization between the time for obtaining a first difference image of the target and a second contrast image of the target after injection with a contrast material is not taken into consideration, the two images cannot be brought together to produce a high quality composite image.

It is therefore an object of the present invention to improve and overcome technical problems recognized with conventional apparatus for photographing and observing three-dimensional targets, such as the cranium region of a living subject.

A further object of the invention is to provide apparatus for continuously photographing and observing a portion of a target area to provide a clear, high-quality, three-dimensional image thereby allowing for a more accurate examination of the target region.

To achieve the aforementioned objects, the present invention includes a transmitting unit for irradiating a certain portion of a target with suitable radiations, an image-receiving unit into which the transmitted radiological rays are incident after passing through a target and which outputs an electrical signal indicative of target image, a holding device for positioning the aforesaid target between the transmitting and receiving units, a drive mechanism for rotating the holding device relative to the transmitting and receiving units, a camera for taking pictures of a first reference image and a contrast image after the target region is injected with a contrast material each time the target is rotated a desired increment, an arithmetic unit for recording digital computations on said images to draw a composite image from each set of reference and contrast images, a memory for recording the first reference image, the second contrast images and the third drawn composite images, first and second image indicators for displaying simultaneously each of the aforesaid drawn composite images taken at different angles, and a synchronizing unit for taking a plurality of pictures of the contrast images of a certain portion of the target for each angular imaging increment, with contrast material injected into the aforesaid certain portion of the target.

In a preferred embodiment of the invention which comprises the apparatus described above, the target is sandwiched between an x-ray unit and the image-recording unit through means of the holding device. The holding device is adapted to rotate around the target in reference to the x-ray unit. For each increment of rotation, a first reference image and a second contrast image are recorded. The timing for injecting contrast material into a certain portion of the target region is synchronized with the x-ray unit by a controller so that high quality composite images of the target can be obtained.

The reference and contrast images are stored in memory and the image data corresponding to both images are differentially computed to obtain a drawn or subtractive composite image of certain portions of the target region for each incremental angle. The drawn composite images are then also stored in memory.

The drawn composite images having certain angle differences are displayed simultaneously on first and second image indicators to achieve a high quality three-dimensional rendition of the target.

These and many other objects, features, and advantages of this invention will become more fully understood from the following detailed description of the invention.

BRIEF DESCRIPTION OF THE DRAWING

FIG. 5 is a descriptive diagram, illustrating a display mode according to the invention.

DETAILED DESCRIPTION OF THE PREFERRED EMBODIMENT

Referring more particularly to the drawings, the invention will now be explained in greater detail.

Figure 1:
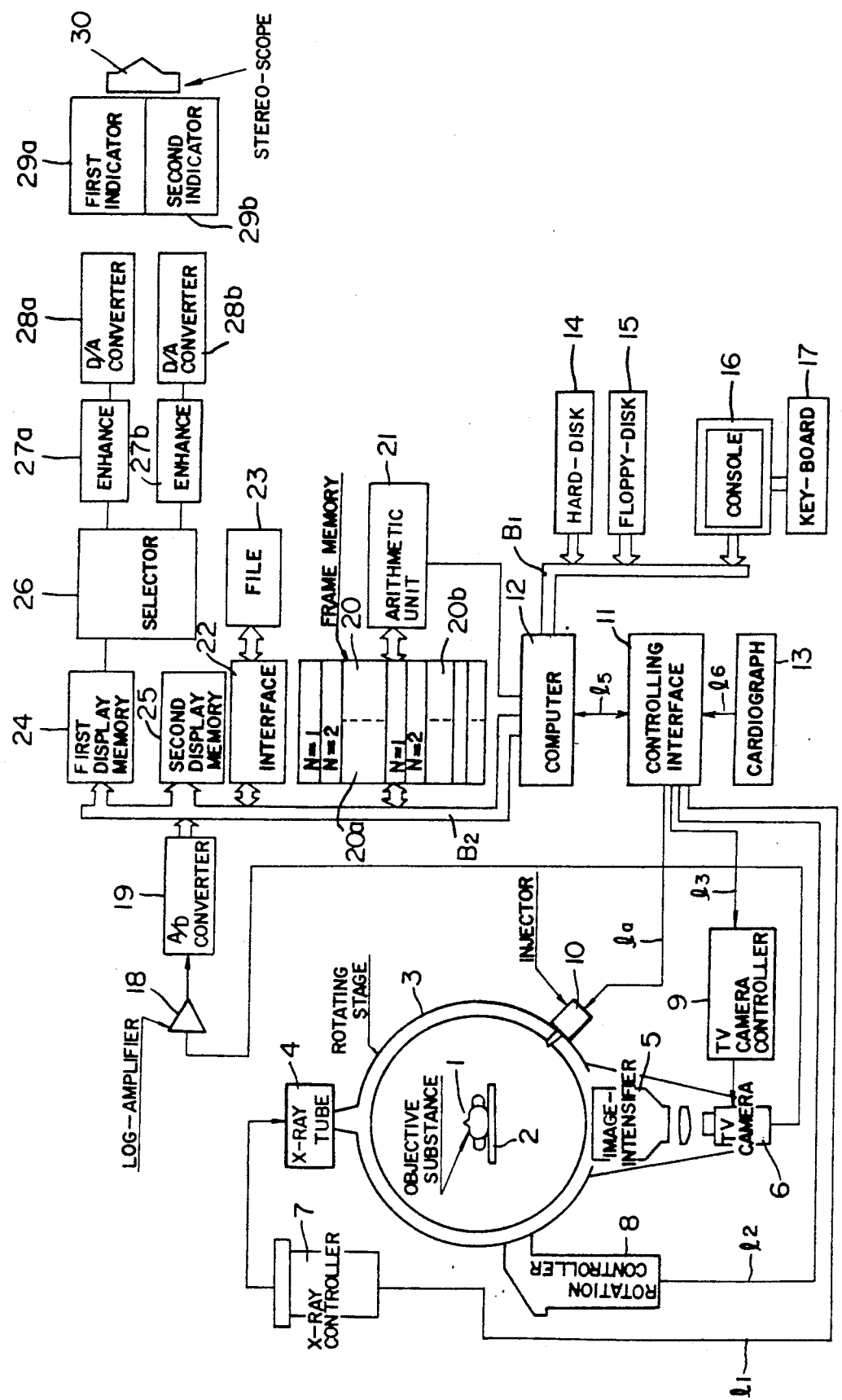
FIG. 1 is a block diagram, illustrating one embodiment of this invention.

FIG. 1 is a block diagram showing a construction of an embodiment of this invention. In this embodiment, an application is demonstrated for recording x-ray transmitted images of certain portions of a target by rotating an x-ray tube and an image-recording unit around the target.

As shown in FIG. 1, a rotating stage 3 is installed so as to rotate freely along the central axis of a target 1 located on a photographing stage 2. The target 1, which may be the skull region of a living subject, is placed on the rotating stage 3 so that it is sandwiched between an x-ray tube 4 and an image recording unit comprised of an image-intensifier 5 and a video camera 6. The x-ray tube 4, the target 1, and the image recording unit are all located along a common axis 32.

An x-ray controller 7 is connected to the x-ray tube 4 and serves to regulate the transmission of radiation from the x-ray tube 4. A rotation controller 8 is also operatively connected to the rotating stage 3 for controlling the angular movement of the rotating stage 3. A video camera controller 9 is connected to video camera 6 to achieve operative control of the camera 6, and an injector 10 is installed to inject the contrast material into certain portions of the target 1.

A controlling interface 11 is coupled with x-ray controller 7, rotation controller 8, video camera controller 9, and injector 10 by means of signal wires $l_1$, $l_2$, $l_3$, and $l_4$ respectively. The controlling interface 11 is connected to a computer 12 through a signal wire $l_5$. The x-ray controller 7, the rotation controller 8, video camera controller 9 and injector 10 are all controlled by a command signal coming from the computer 12.

A cardiograph 13 is connected to the controlling interface 11 through a signal wire $l_6$. The computer 12 is connected to a hard-drive unit 14, a floppy-disk drive unit 15 and an operation console 16 through common buss $B_1$. A keyboard 17 is connected to the operation console 16 to manually address the computer.

An output terminal of the video camera 6 is further connected to an in-put terminal of an amplifier 18. An output terminal of the amplifier 18 is in turn connected to an in-put terminal of A/D converter 19. An output terminal of the A/D converter 19 is connected to a buss $B_2$, to which the computer 12 is connected.

A frame memory 20 is connected to the buss $B_2$ and an arithmetic unit 21 is connected to the frame memory 20. In this frame memory 20, there are two memory zones available. The first memory zone 20a is used to store a first set of digital image signals. These digital image signals are obtained by converting electric signals of recorded reference images from certain portions of the target 1 for each increment of rotation (field) of the rotating stage 3 via the A/D converter 19. The second memory zone 20b is also used to store a second set of digital image signals. The second set of signals are obtained by converting electric signals of recorded contrast images for each aforementioned field through the A/D converter 19.

A file 23 is connected to an interface 22 through the buss $B_2$, to which a first display memory 24 and a second display memory 25 are connected. An out-put terminal of the first display memory 24 and that of the second display memory 25 are connected to an input terminal of a selector 26. Each output terminal of the selector 26 is connected to an input terminal of a first indicator 29a and to an input terminal of a second indicator 29b, so that a three-dimensional observation can be achieved by using a stereo-scope 30.

According to this embodiment of the invention, the x-ray tube 4 and the x-ray controller 7 form a transmitting unit for transmitting a radioactive ray at the target. Image intensifier 5 and video camera 6 define an image-recording unit. Rotating stage 3 serves as a holding means in regard to the target and rotation controller 8 serves as a drive for turning the stage. Computer 12, controlling interface 11, video camera controller 9, rotation controller 8, x-ray controller 7, and an injector 10 define a camera control unit.

An arithmetic unit 21 is used as a computation unit and frame memory 20 serves as a storage unit in the system. Computer 12 and controlling interface 11 define a synchronizing unit.

In the following, a function and operation of the invention are described in greater detail.

The present apparatus is basically operated by installing a hard-disk drive unit 14 and a floppy disk drive unit 15 for sending command signals to computer 12 to position target 1, on the photographing stage 2, attach cardiograph 13 to the target 1, input the cardiac pulse from the target 1 into controlling interface 11, and enable a keyboard 17 of a console 16.

As a first step, a reference image of a desired portion of the target 1 is read into the present equipment.

When the apparatus is initiated after operating the keyboard 17 to set in a desired angular speed Sr (degree/second), the rotating stage 3 is synchronized to a vertical synchronizing signal from the video camera 6 and it begins to rotate. After a certain angular speed Sr is reached, a read-in operation for the reference image is initiated at a starting read-in angle Ds (degree/second) to obtain an image of a desired region of the living target.

Before a starting read-in angle Ds (degree) is achieved, a preliminary radiation check of the x-ray tube 4 is performed according to a preliminary radiation command from the computer 12, which is synchronized to the vertical synchronizing signal of the video camera 6. This stabilizes the high voltage circuit of the x-ray controller 7.

After the high voltage circuit of the x-ray controller 7 is stabilized, the desired rotating angular speed Sr (degree/second) is reached and the rotating stage 3 is at a starting read-in angle Ds (degree), radiation from the x-ray tube 4 starts to irradiate the certain portion of the target 1, in response to a radiation control signal from the computer 12. The control signal is synchronized to the aforementioned vertical synchronized signal, to step the rotating stage 3 a desired number of degrees (for example five degrees for each increment of rotation).

The radiation image from that portion of the target 1 is then converted into an optical image through image intensifier 5. The optical image is recorded by the video camera 6 and converted to an electrical signal. The electrical image signal is applied to an A/D converter 19 through amplifier 18, so that the electrical signal of received image is then converted into a digital image signal.

Recording a reference image of a certain portion of the target 1 by the x-ray radiated from the x-ray tube 4 is achieved for each increment of rotating (five degrees) of stage 3. A digital image signal obtained by the first starting read-in angle Ds (degrees) is written-in to the first field of a frame memory 20 and then another digital image signal obtained from another angle (Ds +5 degrees) is similarly written-in to the second field of the frame memory 20.

In a similar way, a reference image for each increment of rotation is obtained and written-in to the third field, the fourth field, etc. of the frame memory in a sequential manner.

Numbers of read-in reference image, Nfl, can be expressed by the next equation:

$$Nfl = (D_E - D_S) Sr Tfl \qquad (1)$$

where:
  Sr indicates a rotating angular speed of the rotating stage,
  Tfl (sec) the time required for each increment of rotation,
  $D_E$ indicates a final read-in angle, and
  $D_S$ the starting read-in angle.

In the above manner, for example, when ninety sheets of reference images are completed, the rotating stage 3 will have rotated through 360 degrees and thus returned to its original starting position. At this time, a read-in operation for the contrast images is initiated. At the start of this sequence, a suitable contrast material is injected into a certain portion of the target 1 under predetermined conditions.

Figure 4:
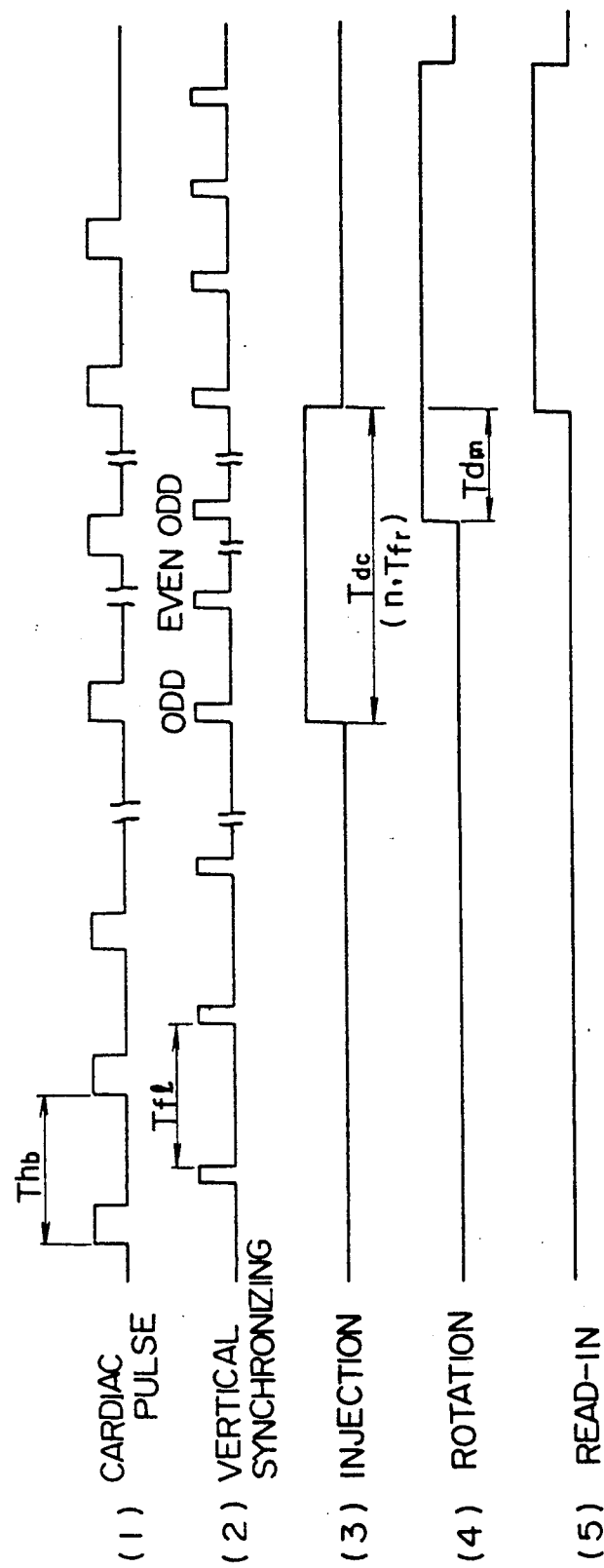
FIG. 4 is a time chart showing the timing for injecting a contrast material into a certain portion of a target.

FIG. 4 illustrates a time chart for timing the injecting of the contrast material according to one embodiment of the invention. The time span, $T_{ds}$, between a completion of an injection of the contrast material and rotating the rotation stage 3 can be defined as $$T_{ds} = T_{dc} - T_{dm} \tag{2}$$

where:
  $T_{dc}$ can be defined as a time required for an injected contrast material to reach a certain target region, and
  $T_{dm}$ is a time required for the starting read-in angle to be reached after rotation is initiated.

The start of a rotation can be defined by the start-up time of the rotating stage 3 and the starting read-in angle.

Hence, if one starts to rotate the rotating stage at $T_{ds}$ as defined by equation (2), after the time of injection, the contrast imaging will be synchronized through the cardiac pulse so that a contrast image of a previously recorded reference image area will also be recorded. As will be explained below, the two corresponding images can be brought together to produce a high quality rendition of the target.

Following the first contrast image, subsequent contrast images can be obtained in the same manner for each increment of rotation. According to the same process noted in reference to the aforesaid reference images, the obtained contrast images are converted to digital image signals by A/D converter 19 and then the first field of each converted signal is written into the second memory zone 20b of the frame memory 20 sequentially up to, for example, the ninetieth field.

When a write-in operation of the reference image into the first memory zone 20a of the frame memory 20 and the write-in operation of the contrast image to the second memory zone 20b of the frame memory 20 are completed, an arithmetic unit 21 is activated by a command from the computer 21. At this time a differential computation is performed between fields corresponding to the second memory zone 20b and the first memory zone 20a. Computed data thus obtained is written into the first memory zone 20a as data from which a drawn or composite image is generated in place of the reference image data.

Figure 2:
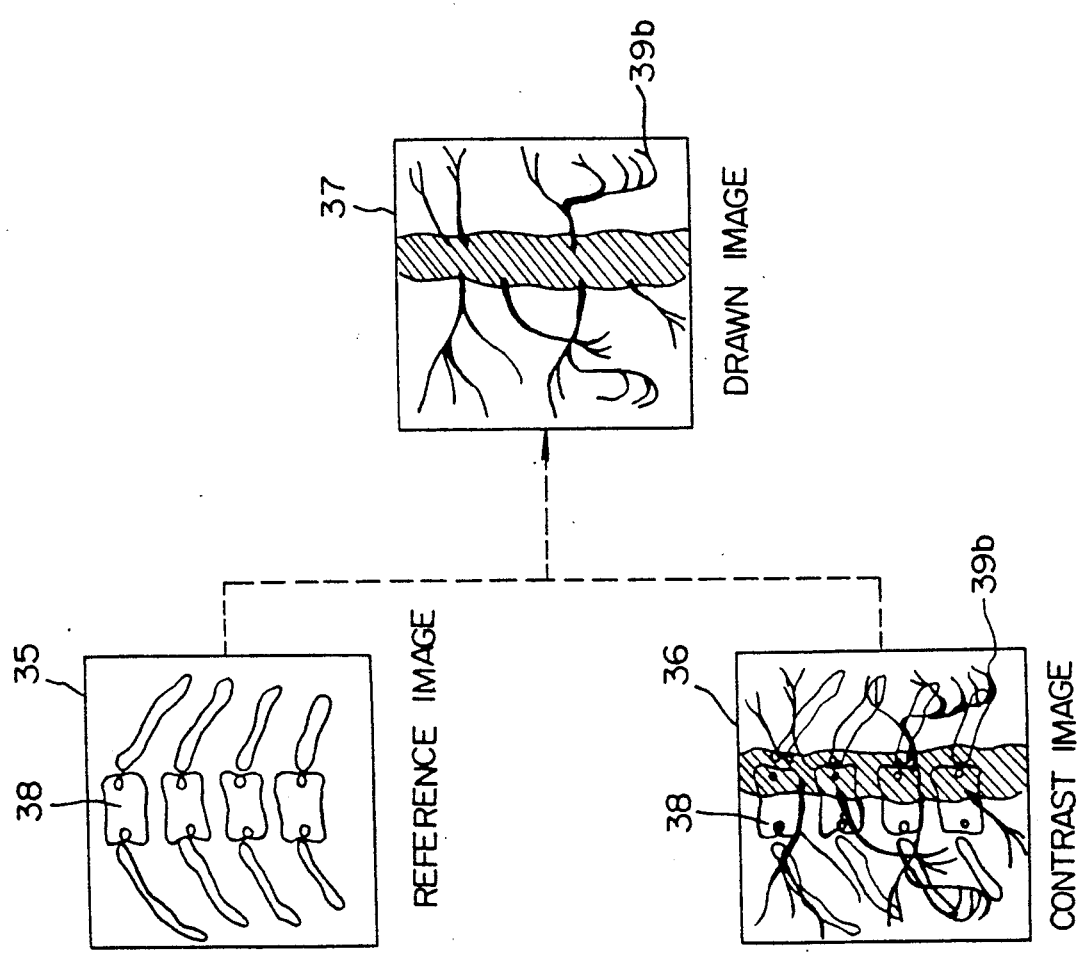
FIG. 2 is a descriptive diagram of a differential drawn composite image computed according to the invention.

FIG. 2 shows a contrast image 36, a reference image 35 and a drawn or composite image 37. The latter is obtained by operating a differential computation of the contrast images 36 and reference images 35. As shown clearly in FIG. 2, the drawn image 37, which is obtained through the operation of arithmetic unit 21, reveals a clear, high-quality image of vessel parts 39b. The transmitted image of bone parts 38 have been cancelled while the transmitted image from vessel parts 39b, which are injected with a contrast material, are clearly visible.

According to this embodiment of the invention, a pair of drawn images 37 having a certain degree of angle difference are displayed simultaneously on the first indicator 29a and on the second indicator 29b to obtain a three-dimensional rendition. It is necessary to have five degrees to seven degrees as a view difference between the left and right eyes to achieve a successful three-dimensional observation. By using Sr and Tr defined by equation (1), numbers of page, an corresponding to this view difference can be given by the following equation:

$$\Delta n = \Delta \theta / (SrTfl) \tag{3}$$

where:
  $\Delta \theta$ indicates a view angle difference.

If SrTfl = 1.25 degrees and $\Delta \theta = 5$ degrees, then $\Delta n = 4$. Therefore, when an image of the first field is required to display on the first indicator 29a, the image of the fifth field is displayed on the second indicator 29b in order to produce a three-dimensional rendition.

Accordingly, for displaying the drawn image, the digital image signal is written into the first display memory 24 from the first memory zone 20a where the digital image signal of the drawn image at the frame memory 20 is selected through selector 26, and then displayed on the first indicator 20a through enhancer 27a and D/A converter 28a, sequentially.

Moreover, the digital image signal of the fifth field (page 5) is written into the second display memory 25 from the first memory zone 20a at the frame memory 20 and displayed on the second indicator 29b after being selected by the selector 26 and processed by enhancer 27b as well as D/A converter 28b. Since these display operations are repeated, the first display memory 24 and second display memory 25 enable a read-after-write operation at a video rate.

In the next step, a digital image signal of the fifth field (page 5) which is written into the second display memory 25 is read-out by the selector 26 and is displayed on the first indicator 29a through enhancer 27a and D/A converter 28a. The digital image signal of the ninth field (page 9) is read out to the second display memory 25 from the first memory zone 20a on the frame memory 20 and is displayed on the second indicator 20b after being selected by the selector 26.

Similarly, the digital image signal is written into the display memory 24 and 25 alternately for every fourth field (page 4) from the first memory zone 20a on the frame memory 20. The digital image signal is then read-out from the first display memory 24 and second display memory 25 alternately through the selector 26, so that they are displayed alternately on the first indicator 29a and second indicator 29b.

In this manner, the drawn image from a certain portion of a target 1 having a five degree angle difference (or view difference) is displayed simultaneously and sequentially on the first indicator 29a and the second indicator 29b. By observing the drawn image displayed on the first indicator 29a and the second indicator 29b using a stereo-scope 30, a continuous observation of the three-dimensional transmitted image from a certain portion of the target at each rotating unit angle can be achieved with high accuracy.

Selection of the direction of fields (pages) at the first memory zone 20a of the frame memory 20 can be changed by operating the keyboard 17. Repeated displays can also be achieved by going forward and backward between certain fields.

FIG. 5 illustrates a selecting display of a certain portion according to the embodiment of the invention. FIG. 5(1) demonstrates a repeated display in which the eighty-first field (page 81) of the first memory zone 20a at the frame memory 20 is treated as a center for recycling display operation.

FIG. 5(2) shows a case when a repeated display along one direction is demonstrated from the first field (page 1) to the eighty-first field (page 81) at the first memory zone 20a on the frame memory 20; while FIG. 5(3) illustrates a case when a normal display from the first field (page 1) to the twenty-fourth field (page 24) is operated, at the twenty-fifth field (page 25) the display is reversed. At the ninth field (page 9) the display is back to the normal direction, and then at the twenty-ninth field (page 29) the display is again reversed.

In these examples of display fields (pages) read into the first indicator 29a and the second indicator 29b are reversed according to clockwise or counter-clockwise direction, so that a face-back relation of the transmitted image from a certain portion of the target is not reversed.

Figure 3:
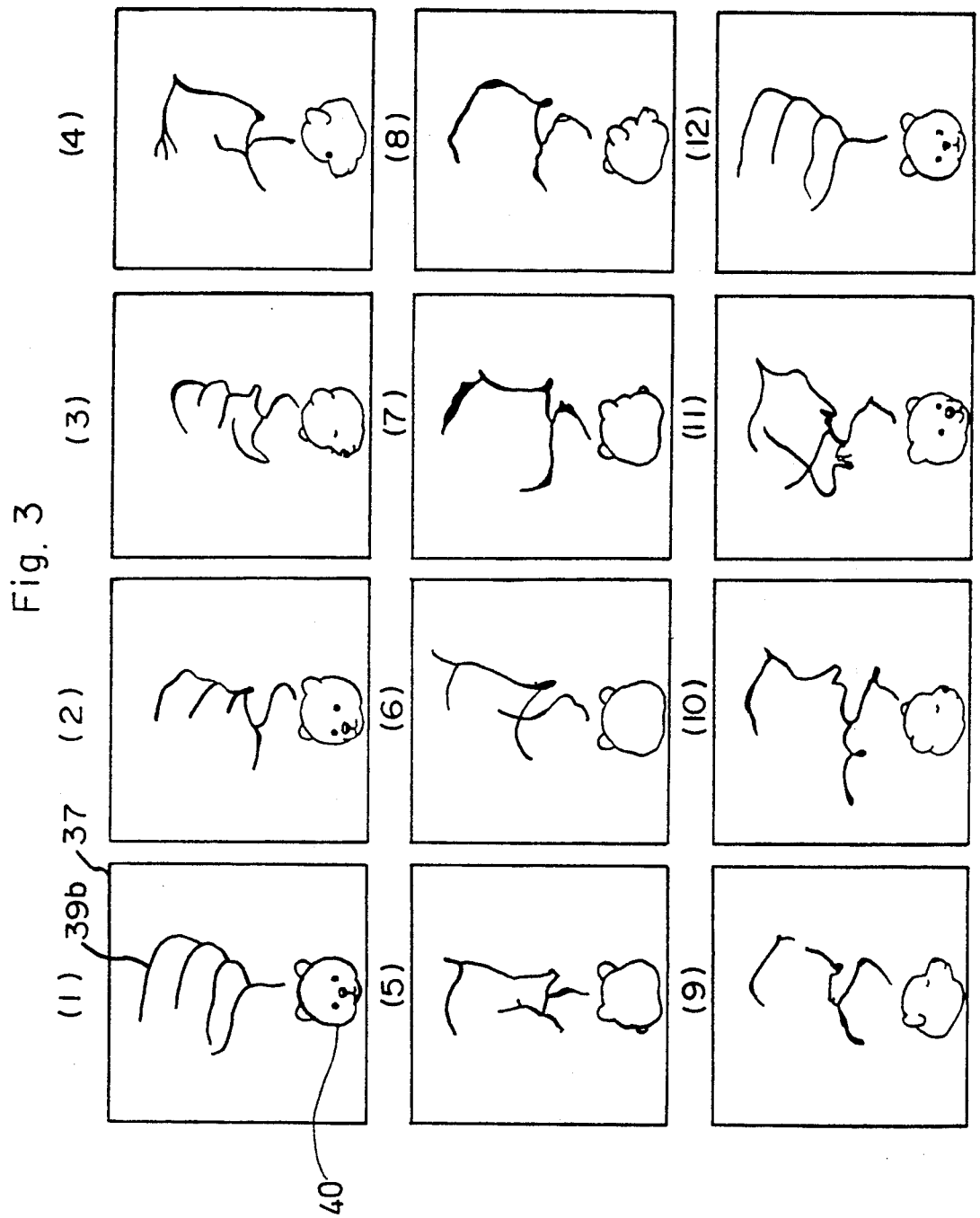
FIG. 3 is a descriptive diagram of an example of a displayed three-dimensional image related to the invention.

FIGS. 3(1) through (12) demonstrate observed renditions of drawn images 37 from certain target portions by a stereo-scope, where the rotating stage 3 is rotated one full turn in a counter-clockwise direction. Images for each thirty degrees are displayed on the first indicator 29a and the second indicator 29b. Corresponding images of a panda's head 40, to provide a reference mark, are attached. Since each image of panda represents a direction of the target 1 for each obtained image, a proper observation of a continuous displaying of a certain target region by using a stereo-scope can be easily recognized.

For displaying these images on the first indicator 29a and the second indicator 29b, a contrast can also be controlled by operating enhancers 27a, 27b using a mouse.

In the above, a detailed displaying of the drawn image is described. Similarly, a reference image or contrast image obtained from a certain portion of the target 1 can also be displayed on the first indicator 29a or the second indicator 29b to perform a three-dimensional observation using the stereo-scope.

Drawn images, contrast images or reference images which are memorized in the frame memory 20 can also be written in on optical-disk or floppy-disk at file 23 through means of the interface 22.

According to the invention, while observing the menu display on the console 16 and obtaining a desired drawn image from a certain portion of the target 1 by operating a keyboard 17 or a mouse, the drawn image can be displayed and observed in a three-dimensional view by a stereo-scope at various modes including (1) continuous display mode for repeated displaying the images (2) head-shaking mode for desired ranges of angles, or (3) head-shaking/rotating mode for moving forward and backward between predetermined angles.

Diagnosis on a certain portion of the target 1 can be achieved by a three-dimensional observation under various selected modes. If desired, a similar three-dimensional observation can be performed on a reference image or contrast image obtained from a certain portion of the objective substance to provide important information between a certain target area and surrounding areas as a supplementary reference for use in a more accurate diagnosis.

Furthermore, since the embodiment of the invention considers synchronizing the timing between injecting a contrast material into a certain portion of the target and photographing this region, a contrast image with extremely high quality can be obtained. An accurate stereoscopic three-dimensional observation on the drawn image, which is based on high quality contrast image, can also be achieved. By synchronizing the starting read-in time for reference and contrast images with the cardiac pulse of the subject 1, images can be obtained under an identical pulse conditions.

The rotating direction of photographing is clearly shown by examining the panda's image for displaying transmitted image from a certain portion by the first indicator 29a or the second indicator 29b, so that the face and the back of the subject target 1 are displayed for a proper three-dimensional presentation.

Although this embodiment of the invention relates to a method by which the target is stationary and the apparatus for producing an image is rotated around the target, an alternate method can also be achieved by which both apparatus for producing an image are fixed and the target is rotated.

While this invention has been explained with reference to the structure disclosed herein, it is not confined to the details as set forth and this application is intended to cover any modifications and changes as may come within the scope of the following claims.

What is claimed is:

1. Apparatus for continuously producing steroscopic pairs of images of a target for viewing that includes
    means for supporting a target upon a common axis between a transmitter means for irradiating the target and an imaging means for recording two-dimensional radiation images of said target and providing electrical data signals of said recorded images,
    stage means for producing relative rotation between the target and the transmitter and imaging means so that images of that target may be recorded at uniform angular increments separated by a predetermined number of degrees,
    memory means connected to the imaging means for storing target image data during each angular increment of rotation,
    injection means for introducing a contrast material into the target at an interval after the start of rotation,
    control means connected to the imaging means and the memory means for causing a target image to be recorded and forwarded to the memory means for storing during each angular increment of rotation before injection of said contrast rotation so that a first set of reference images are stored in the memory means and also after injection of said contrast rotation so that a second set of contrast images are also stored in the memory means,
    arithmetic means associated with said memory means for producing a subtractive drawn image from the reference and contrast image data stored in the memory means for each angular increment of rotation and storing said drawn images in said memory means, and display means connected to the memory means for simultaneously presenting two drawn images for two respective angular increments of rotation of the target for viewing stereoscopically, one to the left eye of an observer and the other to the right eye of the observer, said two drawn images being angularly displaced a predetermined number of degrees so that a stereoscopic picture of the target is presented to the observer.

2. The apparatus of claim 1 wherein said steroscopic display means include a first indicator means for displaying a first drawn image and a second indicator means for displaying a second drawn image, said drawn images being angularly displaced from each other by five to seven degrees of rotation.

3. The apparatus of claim 2 wherein the angle of rotation of each angular increment is equal to the predetermined number of degrees separating the two drawn images displayed by the indicator means.

4. The apparatus of claim 2 wherein said display means further include a selector means for permitting the drawn images to be scanned from said memory means through a desired number of degrees of rotation in either a clockwise or counter-clockwise direction.

5. The apparatus of claim 1 wherein said transmitting means irradiates the target with x-rays.

6. The apparatus of claim 1 wherein the arithmetic means includes means for subtracting contrast image data stored in said memory means from the corresponding reference image data stored in said memory means.

7. The apparatus of claim 1 wherein said control means is included in a computer means for coordinating the operation of the transmitter means, the imaging means, the injecting means, the stage means, the arithmetic means, and the display means.

8. The apparatus of claim 7 wherein said computer means further includes a hard disk or a floppy disk for programming said operations in an ordered sequence.

9. The apparatus of claim 1 wherein said imaging means includes a video camera and further includes means for synchronizing the rotating angle of the stage means with the vertical synchronized signal of the video camera prior to the stage reaching a starting angle at which images of the target are recorded.

10. The apparatus of claim 9 having further means for synchronizing the operation of the transmitter means with the vertical synchronizing signal of said video camera.

11. The apparatus of claim 1 wherein said memory means further includes a first memory zone for storing digital image data relating to the reference images and a second memory zone for storing digital image data relating to the contrast images.

12. The apparatus of claim 2 wherein the display means further includes a stereo-scope connected to said first and second indicator means.

13. The apparatus of claim 4 wherein said display means further includes means for indicating the direction of rotation of the stage means when target images are being displayed.

14. The apparatus of claim 8 wherein the target is a vivos subject and the computer means is programmed to allow the contrast material to flow into the target region before recording said contrast images.

15. The apparatus of claim 1 that includes the further steps of selectively scanning the memory in one direction to produce a clockwise rotation of the picture and in the opposite direction to produce a counter-clockwise rotation of the picture.

16. The apparatus of claim 1 wherein the angular separation between the two displayed drawn images is equal to the angular displacement between increments.

17. The apparatus of claim 1 wherein said display means further includes a reference means for visually indicating a direction of rotation of the target that is being viewed.

18. The apparatus of claim 17 wherein said reference means provide visual indication of the position of the stereoscopic picture relative to the back side and the front side of the target that is being viewed.

19. A method for continuously producing three-dimensional images of a target for viewing that includes the steps of rotating the target in angular increments in relation to a video camera for recording two-dimensional radiation images of the target and providing digital image signals of said target images irradiating the target during each angular increment to produce a series of two-dimensional reference images, storing the reference images in memory, injecting a contrast material into the target, repeating the rotating and irradiating steps to produce a second series of two-dimensional contrast images.

storing the contrast images in memory, performing digital computations on the stored corresponding reference and contrast images to produce an enhanced image of the target for each angular increment of target rotation, storing the enhanced images in memory, and simultaneously displaying two of said enhanced images of the target for respective angular increments and which are angularly displaced a desired number of degrees to produce a stereoscopic picture of the target with one image being presented to the left eye of an observer and the other image being presented to the right eye of the observer.

20. The method of claim 19 that further includes scanning the memory to produce rotation of the stereoscopic picture.

* * * * *